(12) United States Patent
Giori et al.

(10) Patent No.: US 8,372,445 B2
(45) Date of Patent: Feb. 12, 2013

(54) GRAPE SEEDS EXTRACTS OBTAINABLE BY FRACTIONING ON A RESIN

(75) Inventors: Andrea Giori, Milan (IT); Alessandro Anelli, Milan (IT)

(73) Assignee: Indena S.p.A., Milan (IT)

( * ) Notice: Subject to any disclaimer, the term of this patent is extended or adjusted under 35 U.S.C. 154(b) by 497 days.

(21) Appl. No.: 11/989,556

(22) PCT Filed: Jul. 13, 2006

(86) PCT No.: PCT/EP2006/006852
§ 371 (c)(1),
(2), (4) Date: Feb. 17, 2009

(87) PCT Pub. No.: WO2007/017037
PCT Pub. Date: Feb. 15, 2007

(65) Prior Publication Data
US 2009/0202667 A1 Aug. 13, 2009

(30) Foreign Application Priority Data
Jul. 29, 2005 (IT) .............. MI2005A1485

(51) Int. Cl.
*A61K 36/87* (2006.01)
*A61K 36/00* (2006.01)
*B01D 3/00* (2006.01)
*B01D 11/00* (2006.01)

(52) U.S. Cl. ........ 424/725; 424/766; 424/777; 210/633; 210/634; 210/638

(58) Field of Classification Search .................. 424/725, 424/777; 210/633, 634, 638
See application file for complete search history.

(56) References Cited

U.S. PATENT DOCUMENTS 5,814,494 A * 9/1998 Ariga et al. .................... 435/118
2004/0156925 A1 8/2004 Howell et al.
2008/0249163 A1* 10/2008 Takagaki et al. .............. 514/456

FOREIGN PATENT DOCUMENTS

| EP | 0 348 781 A2 | 1/1990 |
| FR | 2 092 743 A1 | 1/1972 |
| GB | 1 541 469 A | 2/1979 |
| JP | 09220055 A * | 8/1997 |

* cited by examiner

*Primary Examiner* — Patricia Leith
(74) *Attorney, Agent, or Firm* — Porzio, Bromberg & Newman, P.C.

(57) ABSTRACT

A process for the extraction of *Vitis vinifera* seeds which comprises:
a) extraction of grape seeds with a solvent (total extract);
b) removal of water-insoluble tannins;
c) optional removal of water-soluble tannins;
d separation of the products with different MW, through chromatographic purification on a column.

5 Claims, No Drawings

GRAPE SEEDS EXTRACTS OBTAINABLE BY FRACTIONING ON A RESIN

The present invention relates to an extract of grape seeds obtainable by fractioning on a resin and to the process for its preparation.

The process of the invention provides an extract starting from grape seeds with variable contents in catechins and epicatechins (monomers). The products obtainable according to the invention have antioxidant action and are mainly used as cosmetics, food supplements (particularly as cardioprotective supplements) and nutraceuticals.

TECHNOLOGICAL BACKGROUND

The total extract obtained from workup of grape seeds contains a number of metabolites, particularly catechin and epicatechin monomers, related proanthocyanidole oligomers and polymers (procyanindins), as well as polymers and high molecular weight tannins.

EP 275224 discloses a process for the preparation of phospholipid complexes of *Vitis vinifera* flavonoids.

WO 2005/36988 discloses a process for the extraction of *Vitis vinifera* seeds consisting in the separation of the skin from the seeds immediately after the workup of the extract. The resulting extracts are characterized by a low content in monomeric polyphenols.

EP 348781 discloses fractions enriched in procyanidol oligomers obtained by extraction of *Vitis vinifera* seeds with ethers or esters or mixtures of esters with aromatic hydrocarbons and/or by filtration.

EP 1035859 discloses the use of phospholipid complexes of extracts of *Vitis vinifera* for the treatment and the prevention of atherosclerosis.

The known processes have some drawbacks, such as the use of toxic solvents or the need of specific plants or complex procedures.

There is therefore the need of a convenient process, which is industrially carried out in a easy way and provides extracts whose contents in active components may be adjusted at will.

DISCLOSURE OF THE INVENTION

The process of the invention is flexible as it allows to separate a number of fractions that differ in the molecular weights (MW) of the catechin and epicatechin derivatives therein contained This process thereby allows to prepare both catechin- and epicatechin-enriched extracts with a reduced content in proanthocyanidole oligomers and polymers (procyanindins), and extracts with diametrically opposed characteristics, i.e. having high contents in oligomers and procyanindins and reduced contents in monomers (catechin and epicatechin), as well as extracts having any desired contents in monomers and procyanindins.

Such flexibility also concerns the possibility of mixing these different fractions to obtain final products with a predetermined monomer content.

High molecular polymers and tannins contained in the total extract are removed from the desired fractions in the first workup steps by partial purification in water, which can be optionally optimized by subsequent treatment with polyvinylpolypyrrolidone (PVPP).

The partial purification in water removes only part of the tannins (more than 50% w/w), but only PVPP purification reduces the tannins content to less than 5% of the final extract weight.

This invention differs from the prior art processes for the preparation of products derived form grape seeds in the following fundamental features:
i. The extraction of grape seeds is carried out without need of pH control, as neither basic nor acidic chemicals are used.
ii. The extraction and the whole productive process can be carried out using only water and ethanol as solvents.
iii. The process is flexible as it allows to adjust at will the final extract contents in monomers and oligomers.
iv. High molecular weight polymers and tannins are removed.

As a whole, the process of the invention involves four main steps:
a) Extraction of grape seeds with a solvent (total extract);
b) Removal of water-insoluble tannins;
c) Optional removal of water-soluble tannins;
d) Separation of the products with different MW, through chromatographic purification on a column (this step can also be carried out directly on any solution resulting from step b, without the need to carry out also step c).

Step (a) is effected by extraction of grape seeds with acetone or a $C_1$-$C_3$ alcohol, or mixtures or aqueous solutions thereof solvents as long as water content does not exceed 90% (v/v). A 40% v/v water-ethanol solution is preferred.

The extraction temperature can range from 0° C. to the boiling solvent temperature, and is preferably 70° C.

Step (b), which allows to remove water-insolubles, particularly high molecular weight tannins, from the extract, is effected cooling the extract from step (a) and filtering or centrifuging off the insolubles.

Step (c) is an optional step, which can be carried out to remove any tannins still present in the extract from step (b). These metabolites can be removed by using polyvinylpolypyrrolidone (PVPP).

Preferably, the process of the invention comprises also step (c).

Step (d) allows to fractionate the extract removing most useless secondary metabolites (sugars and the like), while keeping procyanindins. This step consists in a chromatographic separation through adsorption on a polymeric resin. Examples of suitable resins for this purpose are styrene-DVB resins such as AmberliteHP20® or Rohm and Haas XAD1180®, or acrylic resins such as Rohm and Haas XAD7HP®.

The total extract obtained from grape seeds is concentrated to a dry residue ranging from 5% to 50% w/w, preferably 10% w/w, and is left to stand at a temperature ranging from 1° C. to 25° C., preferably at 4° C., without stirring, for a time ranging from 1 hour to 24 hours, preferably 16 hours.

The resulting suspension is centrifuged at 4° C. until removing the residual precipitate from the aqueous solution. The clear aqueous solution is concentrated in a rotary evaporator and water is added to obtain a dry residue ranging from 5% to 50% w/w, preferably 10% w/w. In some cases, the solution can be either water-alcohol or water-acetone, instead of only aqueous. This depends on the desired finished product: for instance, when a product with high content in catechin monomers and oligomers is desired, an aqueous solution is preferably used, otherwise either the water-alcohol or water-acetone solutions are used.

Therefore, when low molecular fractions are to be removed from the final product, the solution to load onto the column should have a dry residue ranging from 5% to 50% w/w, as well as an alcohol (C1-C3 alcohols) or acetone content ranging from 5% to 30% v/v, preferably 10% v/v. The thereby prepared solution is adsorbed on the resin, while the unretained solution is removed.

After that, the resin is washed with a water-alcohol ($C_1$-$C_3$ alcohols, preferably ethanol) or water-acetone solution to remove undesired secondary metabolites. The solvent should have a water content ranging from 100% to 70% v/v, preferably 90% v/v. The washing solution exiting from the column is discarded.

The product is eluted with a water-alcohol solution (C1-C3 alcohols), preferably with ethanol, with a water content ranging from 50% to 5% v/v, preferably 30% v/v. The alcohol solution can optionally be replaced with a water-acetone solution with a water content ranging from 50% to 0% v/v, preferably 30% v/v.

The invention is described in greater detail in the following examples.

EXAMPLE 1

Extraction of Grape Seeds With A Water-Alcohol Solution (Step A)

In this step, the total extract used as the starting material for the subsequent column chromatography separation, is prepared.

1000 g of grape seeds are covered with 1.5 liters of ethanol (40% v/v) at 70° C. for 4 hours in a jacketed static percolator. After 4 hours the percolate is recovered and extracted 7 times again under the same conditions, but using 1 liter of solvent for each extraction, to obtain approx. 8 liters of total percolate. The combined percolates are hot filtered with suction and concentrated by rotary evaporator at 60° C. under reduced pressure. This extract has a total dry residue of 228 g, the yield on the starting material being 22.8% w/w. The percolate is concentrated to obtain 2.28 kg of a totally aqueous suspension with 10% w/w dry residue.

EXAMPLE 2

Extraction of Grape Seeds With A Water-Acetone Solution (Step A)

In this step, the total extract which can be used as the starting material for the subsequent column chromatography separation, is prepared.

1000 g of grape seeds are covered with 1.5 liters of acetone 40% v/v at 70° C. for 4 hours in a jacketed static percolator or in a jacketed reactor equipped with stirrer. After 4 hours the percolate is recovered and extracted 7 times again under the same conditions, but using 1 liter of solvent for each extraction, to obtain approx. 8 liters of total percolate. The combined percolates are hot filtered with suction and concentrated by rotary evaporator at 60° C. under reduced pressure. This extract has a total dry residue of 235.6 g, the yield on the starting material being 23.56% w/w.

The percolate is concentrated to obtain 2.35 kg of a totally aqueous suspension with a dry residue of 10% w/w.

EXAMPLE 3

Purification of the Extract Obtained From Grape Seeds (Step B): Removal of Water-Insolubles The aqueous suspension resulting from the water-alcohol extraction of step (a) (Example 1) is cooled at 4° C. and left to stand for 16 hours, then the still cold aqueous suspension is centrifuged at 3000 g for 20 minutes to separate the precipitated residue from the clear aqueous solution. The residue, rich in high molecular products, is discarded.

The resulting clear solution has a dry residue equivalent to 168 g of partially purified extract having catechin HPLC content of 3.75%, and epicatechin HPLC content of 2.87%, and monomers total content (catechin+epicatechin) of 6.62% w/w. The weight yield on the starting material is 16.8% w/w.

All the chromatographic column purification procedures described hereinbelow (4 different procedures) can be applied to this solution. For sake of brevity, only Example 5 (making use of procedure 1) will be reported by way of example of direct purification of this solution. All the other methods described subsequently will be applied to the PVPP-treated solution.

EXAMPLE 4

Purification of the Extract Obtained From Grape Seeds (Step B): Removal of Water-Insolubles The aqueous suspension resulting from the water-acetone extraction of step (a) (Example 2) is cooled at 4° C. and left to stand for 16 hours, then the still cold aqueous suspension is centrifuged at 3000 g for 20 minutes to separate the precipitated residue from the clear aqueous solution. The residue, rich in high molecular products, is discarded.

The resulting clear solution has a dry residue of 173 g of partially purified extract having catechin HPLC content of 4.21%, epicatechin HPLC content of 2.70% and HPLC monomers total content (catechin+epicatechin) of 6.91% w/w. The weight yield on the starting material of this extract is 17.3% w/w.

All the chromatographic purification procedures described hereinbelow (4 different procedures) can be applied to this solution. For sake of brevity, only Example 6 (making use of procedure 3) will be reported by way of example of direct purification of this solution. All of the other methods described subsequently will be applied to the PVPP-treated solution.

EXAMPLE 5

Purification of the Extract Obtained From Grape Seeds: Procedure 1 (Step D)

The clear aqueous solution having a dry residue of 168 g, obtained at the end of the partial purification process described in step (b) (Example 3), is concentrated to a dry residue of 10% w/w. This clear solution of partially purified extract has a dry residue having catechin HPLC content of 3.75%, epicatechin HPLC content of 2.87% and HPLC monomers total content (catechin+epicatechin) of 6.62% w/w.

This aqueous solution is warmed to room temperature, then loaded onto a chromatographic column containing 3300 ml of Rohm and Haas XAD7HP® resin conditioned with water. The water solution is adsorbed to the resin, while the unretained solution exiting from the column is discarded. The resin is then washed with 6.6 liters of water, removing also this solution as its monomer content is negligible and the procyanindins content is low. These discarded aqueous solutions (product 1) have a total dry residue of 69 g (weight yield on the starting material: 6.9% w/w.), catechin HPLC content of 0.09%, epicatechin HPLC content of 0.10%, the total monomers content (catechin+epicatechin) being 0.19% w/w.

The column is eluted with 9 liters of 90% v/v aqueous ethanol. The resulting eluate is recovered and dried at 60° C. under reduced pressure, to yield 98 grams of dry product (product 2), corresponding to a yield on the starting material of 9.80% w/w. This product has a catechin HPLC content of 6.25%, epicatechin HPLC content of 4.77% and HPLC total monomers content (catechin+epicatechin) of 11.02% w/w.

EXAMPLE 6

Purification of the Extract Obtained From Grape Seeds: Procedure 2 (Step D)

The clear aqueous solution having a dry residue of 173 g, obtained by a water-acetone extraction (step a; Example 2) followed by the partial purification as described in step (b) (Example 4), is concentrated to a dry residue of 10% w/w.

After that, this aqueous solution is brought to room temperature, then loaded onto a chromatographic column containing 3300 ml of Rohm and Haas XAD1180® resin; the unretained solution is removed. The resin is washed with 6 liters of water, and the washing solution is combined with the unretained one. The resulting aqueous solution is dried to obtain product 3, having a dry residue of 99.4 g, catechin HPLC content of 1.29% w/w, epicatechin HPLC content of 0.46% w/w.

The resin is then washed with 6 liters of 10% v/v acetone, the resulting solution is collected and dried (product 4). Said product has a dry residue of 23.9 g, catechin HPLC content of 13.5% w/w, HPLC epicathechin content of 8.41% w/w.

The resin is then washed with 6 liters of 20% v/v acetone, the resulting solution is collected and dried (product 5). Said product has a dry residue of 15.3 g, catechin HPLC content of 14.3% w/w, epicatechin HPLC content of 10.9% w/w.

The resin is then washed with 6 liters of 30% v/v acetone, the resulting solution is collected and dried (product 6). Said product has dry residue of 14.95 g, catechin HPLC content of 2.21% w/w, epicatechin HPLC content of 2.04% w/w.

The resin is then washed with 6 liters of 40% v/v acetone, the resulting solution is collected and dried (product 7). Said product has a dry residue of 14.2 g, catechin HPLC content of 1.06% w/w, epicatechin HPLC content of 0.66% w/w.

The resin is then washed with 6 liters of 50% v/v acetone, the resulting solution is collected and dried (product 8). Said product has a dry residue of 3.51 g, catechin HPLC content of 0.67% w/w, epicatechin HPLC content of 0.46% w/w.

The resulting products can be mixed at will to obtain a product with the desired monomers content. For instance, a product with reduced monomers content can be obtained by mixing 3.51 g of product 8 with 14.2 g of product 7 to obtain 17.71 g of product having catechin HPLC content of 0.98% w/w, epicatechin HPLC content of 0.62% w/w, HPLC total monomers content (catechin+epicatechin) of 1.60% w/w. Alternatively, 3.51 g of product 8 can be mixed with 14.2 g of product 7 and with 15.0 g of product 3 to obtain 32.71 g of a product having catechin HPLC content of 1.12% w/w, epicatechin HPLC content of 0.55% w/w and HPLC total monomers content (catechin+epicatechin) of 1.67% w/w.

On the other hand, a product with high monomers content can be obtained by mixing 23.9 g of product 4 with 15.3 g of product 5, to obtain 39.2 g of product having catechin HPLC content of 13.81% w/w, epicatechin HPLC content of 9.38% w/w, and HPLC total monomers content (catechin+epicatechin) of 23.19% w/w.

EXAMPLE 7

Removal of Water-Soluble Tannins From the Extract Obtained From Grape Seeds (Step C)

The clear aqueous solution obtained from the partial purification of step b (Example 3), having a dry residue of 168 g, is treated to remove water-soluble tannins. The solution is added with 34 g of PVPP, corresponding to approx. 20% w/w of the dry residue weight of the extract to treat.

After stirring for 1 hour at room temperature, PVPP is filtered off through a pleated filter. The resulting solution has a dry residue of 160 g of partially purified extract having a tannin content of 2.7% w/w.

The weight yield on the starting material is 16.0% w/w.

EXAMPLE 8

Removal of Water-Soluble Tannins From the Extract Obtained From Grape Seeds (Step C)

The clear aqueous solution obtained from the partial purification of step b (Example 4) and having a dry residue of 168 g, is treated to remove water-soluble tannins. The solution is added with 52 g of PVPP, corresponding to approx. 30% w/w of the dry residue weight of the extract to treat.

After stirring for 1 hour at room temperature, PVPP is filtered off through a pleated filter.

The resulting solution has a dry residue of 163 g of partially purified extract having a tannin content of 1.5% w/w.

The weight yield on the starting material is 16.3% w/w.

EXAMPLE 9

Purification of the Extract Obtained From Grape Seeds Procedure 1 (Step D)

The clear aqueous solution having a dry residue of 160 g, obtained from the partial purification of step (c) (Example 7), is concentrated to a dry residue of 10% w/w. This clear solution of partially purified extract has a dry residue with catechin HPLC content of 3.87%, epicatechin HPLC content of 2.96% and HPLC total monomers content (catechin+epicatechin) of 6.83% w/w.

This aqueous solution is brought to room temperature, then loaded onto a chromatographic column containing 3200 ml of Rohm and Haas XAD7HP® resin conditioned with water. The aqueous solution is adsorbed to the resin, while the unretained solution exiting from the column is discarded. The resin is then washed with 6.4 liters of water, removing also this solution as its monomers content is negligible and that in procyanindins is low. These discarded aqueous solutions (product 9) have a total dry residue of 65 g (weight yield on the starting material: 6.5% w/w.), catechin HPLC content of 0.09%, epicatechin HPLC content of 0.10%, the monomers total content (catechin+epicatechin) being 0.19% w/w.

The column is eluted with 9 liters of 90% v/v aqueous ethanol. The resulting eluate is recovered and dried at 60° C. under reduced pressure, to yield 95 grams of dry product (product 10), corresponding to a yield of 9.50% w/w on the starting material. This product has catechin HPLC content of 6.34%, epicatechin HPLC content of 4.85% and HPLC total monomers content (catechin+epicatechin) of 11.19% w/w.

EXAMPLE 10

Purification of the Extract Obtained From Grape Seeds: Procedure 3 (Step D)

The clear aqueous solution having a dry residue of 160 g, obtained from the partial purification of step (c) (Example 7), is concentrated to a dry residue of 10% w/w.

This clear aqueous solution is brought to room temperature, then loaded onto a chromatographic column containing 1600 ml of Rohm and Haas XAD1180® resin. The aqueous solution is adsorbed to the resin, while the unretained solution exiting from the column is removed. The resin is then washed with 3 liters of water, collecting the washing solution which is combined with the unretained one. The resulting aqueous solution is dried to obtain (product 11). Said product has dry residue of 106.2 g, catechin HPLC content of 1.39% w/w, epicatechin HPLC content of 0.95% w/w.

The resin is then washed with 3 liters of ethanol (10% v/v), then the resulting solution is collected and dried (product 12). Said product has a dry residue of 12.0 g, catechin HPLC content of 12.0% w/w, epicatechin HPLC content of 7.80% w/w.

The resin is then washed with 3 liters of ethanol (20% v/v), the resulting solution is collected and dried (product 13). Said product has a dry residue of 14.7 g, catechin HPLC content of 11.5% w/w, epicatechin HPLC content of 9.23% w/w.

The resin is then washed with 3 liters of ethanol (30% v/v), the resulting solution is collected and dried (product 14). Said product has a dry residue of 20.0 g, catechin HPLC content of 6.49% w/w, epicatechin HPLC content of 5.76% w/w.

The resin is then washed with 3 liters of ethanol (40% v/v), the resulting solution is collected and dried (product 15). Said product has a dry residue of 5.08 g, catechin HPLC content of 2.84% w/w, epicatechin HPLC content of 2.59% w/w.

The resin is then washed with 3 liters of ethanol (50% v/v), the resulting solution is collected and dried (product 16). Said product has a dry residue of 1.55 g, catechin HPLC content of 0.51% w/w, epicatechin HPLC content of 0.35% w/w.

The resulting products can be mixed at will to obtain a product with the desired monomers content. For instance, a product with reduced monomers content can be obtained by mixing 1.55 g of product 16 with 5.08 g of product 15 to obtain 6.63 g of product having catechin HPLC content of 2.26% w/w, epicatechin HPLC content of 2.11% w/w and HPLC total monomers content (catechin+epicatechin) of 4.37% w/w or 1.55 g of product 16 can be mixed with 7.00 g of product 11 to obtain 8.55 g of a product having catechin HPLC content of 1.19% w/w, epicatechin HPLC content of 0.89% w/w and HPLC total monomers content (catechin+epicatechin) of 2.08% w/w.

On the other hand, a product with a high monomers content can be obtained by mixing 12.0 g of product 12 with 12.0 g of product 13 and with 15.0 g of product 14, to obtain 39.0 g of a product having catechin HPLC content of 9.73% w/w, epicatechin HPLC content of 7.46% w/w and HPLC total monomers content (catechin+epicatechin) of 17.19% w/w, or 12.0 g of product 12 can be mixed with 12.0 g of product 13 to obtain 24.0 g of product having catechin HPLC content of 11.75% w/w, epicatechin HPLC content of 8.52% w/w, and a HPLC total monomers content (catechin+epicatechin) of 20.27% w/w.

EXAMPLE 11

Purification of the Extract Obtained From Grape Seeds: Procedure 4 (Step D)

The clear aqueous solution having a dry residue of 160 g, obtained from the partial purification of step (c) (Example 7), is concentrated to a dry residue 10% w/w.

This clear aqueous solution is concentrated to a dry residue (12% w/w), then added with 320 ml of ethanol (95% v/v), to obtain a dry residue of about 10% w/w and ethanol content of about (20% v/v). This water-alcohol solution is brought to room temperature, then loaded onto a chromatographic column containing 1600 ml of Rohm and Haas XAD1180® resin. The unretained solution exiting from the column is removed. The resin is then washed with 9.60 liters ethanol 20% v/v, also removing the washing solution, having a dry residue of 135.6 g, with catechin HPLC content of 4.37% w/w, epicatechin HPLC content of 3.35% w/w, and HPLC total monomers content (catechin+epicatechin) of 7.72% w/w.

The column is eluted with 6.60 liters of 70% v/v aqueous ethanol, and the eluate exiting from the column is collected and dried at 60° C. under reduced pressure, to yield a product (product 17) with a dry residue of 24.3 g, catechin HPLC content of 0.79% w/w, epicatechin HPLC content of 0.62% w/w, and HPLC total monomers content (catechin+epicatechin) of 1.41% w/w.

EXAMPLE 12

Purification of the Extract Obtained From Grape Seeds: Procedure 2 (Step D)

The clear aqueous solution having a dry residue of 163 g, obtained from the water-acetone extraction of step (a) (Example 2) followed by the partial purification of step (b) (Example 4) and removal of tannins of step (c) (Example 8), is concentrated to a dry residue of 10% w/w.

This clear aqueous solution is brought to room temperature, then loaded onto a chromatographic column containing 3200 ml of Rohm and Haas XAD7HP® resin conditioned with water. The water-alcohol solution is adsorbed to the resin, while the unretained solution exiting from the column is removed. The resin is then washed with 6.4 liters of water, removing also this solution as its monomers content is negligible and that in procyanindins is low. These discarded aqueous solutions (product 18) have a total dry residue of 62.5 g (weight yield vs. starting material: 6.3% w/w.), catechin HPLC content of 0.11%, epicatechin HPLC content of 0.14%, and HPLC total monomers content (catechin+epicatechin) of 0.25% w/w.

The column is eluted with 9 liters of 90% v/v aqueous acetone, and the eluate exiting the column is collected and dried at 60° C. under reduced pressure, to yield 99.8 g of a dry product (product 19) (the yield vs. starting material: 10% w/w). This product has catechin HPLC content of 7.11%, epicatechin HPLC content of 4.52%, and HPLC total monomers content (catechin+epicatechin) of 11.63% w/w.

EXAMPLE 13

Purification of the Extract Obtained From Grape Seeds: Procedure 3 (Step D)

The clear aqueous solution having a dry residue of 163 g, obtained from the water-acetone extraction of step a (Example 2) followed by the partial purification of step (b) (Example 4) and removal of tannins of step c (Example 8), is concentrated to a dry residue of 10% w/w.

This aqueous solution is brought to room temperature, then loaded onto a chromatographic column containing 3200 ml of Rohm and Haas XAD1180® resin conditioned with water.

The aqueous solution is adsorbed to the resin, while the unretained solution exiting from the column is removed. The resin is then washed with 6 liters of water, removing also this solution which is combined with the unretained one. The resulting aqueous solution is dried to a product (product 20). Said product has a dry residue of 106.4 g, catechin HPLC content of 1.58% w/w, epicatechin HPLC content of 0.47% w/w.

The resin is then washed with 6 liters of 20% v/v acetone, the resulting solution is collected and dried (product 22). Said product has a dry residue of 11.7 g, catechin HPLC content of 16.8% w/w, epicatechin HPLC content of 15.2% w/w.

The resin is then washed with 6 liters of 30% v/v acetone, the resulting solution is collected and dried (product 23). Said product has a dry residue of 11.8 g, catechin HPLC content of 2.20% w/w, epicatechin HPLC content of 2.20% w/w.

The resin is then washed with 6 liters of 40% v/v acetone, the resulting solution is collected and dried (product 24). Said product has a dry residue of 10.2 g, catechin HPLC content of 1.15% w/w, epicatechin HPLC content of 0.75% w/w.

The resin is then washed with 6 liters of 50% v/v acetone, the resulting solution is collected and dried (product 25). Said product has a dry residue of 3.04 g, catechin HPLC content of 0.71% w/w, epicatechin HPLC content of 0.43% w/w.

The resulting products can be mixed at will to obtain a product with the desired monomers content. For instance, a product with reduced monomers content can be obtained by mixing 3.04 g of product 25 with 10.2 g of product 24 to obtain 13.24 g of product having catechin HPLC content of 1.05% w/w, epicatechin HPLC content of 0.68% w/w, and HPLC total monomers content (catechin+epicatechin) of 1.73% w/w, or 3.04 g of product 25 can be mixed with 10.2 g of product 24 and with 15.0 g of product 20 to obtain 28.24 g of a product having a HPLC monomers content x of 1.33% w/w, epicatechin HPLC content of 0.57% w/w and HPLC total monomers content (catechin+epicatechin) of 1.90% w/w.

On the other hand, a product with high monomers content can be obtained by mixing 19.6 g of product 21 with 11.7 g of product 22 to obtain 31.3 g of product having catechin HPLC content of 15.80% w/w, epicatechin HPLC content of 11.88% w/w, and HPLC total monomers content (catechin+epicatechin) of 27.76% w/w.

The invention claimed is:
1. A process for the extraction of *Vitis vinifera* seeds consisting of the steps of:
    a) extraction of grape seeds with a C1-C3 alcohol, mixtures thereof or aqueous solutions thereof with a water content not higher than 90% (v/v) to form an extract;
    b) removal of water-insoluble tannins by cooling the extract of step a) and filtering and centrifuging off the insolubles;
    c) removal of water-soluble tannins by adding polyvinylpolypyrrolidone (PVPP) to the extract of step b); and
    d) separation of products in the extract of step c) having different molecular weights, through repeated chromatographic purification on a column to obtain products with predetermined contents of monomers of catechin and epicatechin and predetermined contents of proanthocyanidole oligomers and procyanindins.

2. The process as claimed in claim 1 in which the extraction solvent is a water-ethanol solution 40% v/v.

3. The process as claimed in claim 1 in which the extraction is carried out at 70° C.

4. The process as claimed in claim 1, in which the chromatographic separation is carried out on styrene-divinyl benzene or acrylic resins.

5. A process for the extraction of *Vitis vinifera* seeds consisting of the steps of:
    a) extraction of grape seeds with a C1-C3 alcohol, mixtures thereof or aqueous solutions thereof with a water content not higher than 90% (v/v) to form an extract;
    b) removal of water-insoluble tannins by cooling the extract of step a) and filtering and centrifuging off the insolubles;
    c) removal of water-soluble tannins by adding polyvinylpolypyrrolidone (PVPP) to the extract of step b); and
    d) separation of products in the extract of step c) having different molecular weights, through repeated chromatographic purification on a column to obtain products with predetermined contents of monomers of catechin and epicatechin and predetermined contents of proanthocyanidole oligomers and procyanindins further comprising the step of:
    mixing two or more of the products determined from step d) to obtained a final product with a predetermined content of the monomers.

* * * * *